US009494410B2

(12) United States Patent
Ho et al.

(10) Patent No.: US 9,494,410 B2
(45) Date of Patent: Nov. 15, 2016

(54) METHOD FOR MEASURING CHARACTERISTICS OF SAMPLE

(71) Applicant: NATIONAL TAIWAN UNIVERSITY, Taipei (TW)

(72) Inventors: Tuan-Shu Ho, Taipei (TW); Chien-Chung Tsai, Taipei (TW); Kuang-Yu Hsu, Taipei (TW); Sheng-Lung Huang, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 466 days.

(21) Appl. No.: 14/097,246

(22) Filed: Dec. 5, 2013

(65) Prior Publication Data
US 2015/0160124 A1    Jun. 11, 2015

(51) Int. Cl.
G01B 9/02 (2006.01)
G01B 11/06 (2006.01)
G01N 21/47 (2006.01)

(52) U.S. Cl.
CPC ....... *G01B 9/02091* (2013.01); *G01B 9/02044* (2013.01); *G01B 9/02088* (2013.01); *G01B 11/0675* (2013.01); *G01N 21/4795* (2013.01)

(58) Field of Classification Search
CPC .................................. G01B 9/02091
USPC ........................................ 702/189
See application file for complete search history.

(56) References Cited

U.S. PATENT DOCUMENTS 5,341,205 A * 8/1994 McLandrich ...... G01B 11/0675
356/479
6,545,763 B1 4/2003 Kim et al.
8,379,228 B1 2/2013 Streater
2006/0176494 A1 8/2006 Finarov
2009/0097036 A1* 4/2009 Galle ................. G01M 11/3163
356/477
2011/0051127 A1 3/2011 Kusaka et al.
2013/0182245 A1 7/2013 Yasunaga et al.

FOREIGN PATENT DOCUMENTS

TW             201016193 A      5/2010

OTHER PUBLICATIONS

T. S. Ho et al., "Simultaneous Measurement of Complex Refractive Index and Thickness of Absorptive Film by Spectroscopic Optical Coherence Tomography" OPTIC 2013.
T. S. Ho et al., "Absorptive Thin Film Characterization with Spectroscopic Full-field Optical Coherence Tomography" CLEO 2013.

* cited by examiner

*Primary Examiner* — Bryan Bui
(74) *Attorney, Agent, or Firm* — CKC & Partners Co., Ltd.

(57) ABSTRACT

A method for measuring characteristics of a sample is provided. The method includes the following steps: obtaining an interference spectrum of the sample; transforming the interference spectrum into a temporal interference signal via a Fourier transform, in which the temporal interference signal includes a plurality of coherence wave packets; separating the wave packets; transforming the wave packets into a plurality of interface interference signals via an inverse Fourier transform; and fitting a plurality of factors of the interface interference signals into a model for obtaining the refractive indexes, the extinction coefficients, and a thickness of the sample.

12 Claims, 8 Drawing Sheets

METHOD FOR MEASURING CHARACTERISTICS OF SAMPLE

BACKGROUND

Optical coherence tomography (OCT) is an optical signal acquisition and processing method. It captures micrometer-resolution, three-dimensional images from within optical scattering media (e.g., biological tissue). Optical coherence tomography is an interferometric technique, typically employing near-infrared light. The use of relatively long wavelength light allows it to penetrate into the scattering medium.

Light in an OCT system is broken into two arms—a sample arm (containing the sample) and a reference arm (usually a mirror). The combination of reflected light from the sample arm and reference light from the reference arm gives rise to an interference pattern if light from both arms has traveled the "same" optical distance ("same" meaning a difference of less than a coherence length).

By scanning the mirror in the reference arm, a reflectivity profile of the sample can be obtained. Areas of the sample that reflect back a lot of light will create greater interference than areas that don't. Any light that is outside the short coherence length would not interfere. This reflectivity profile, called an A-scan, contains information about the spatial dimensions and location of structures within the sample. A cross-sectional tomograph (B-scan) may be achieved by laterally combining a series of these axial depth scans (A-scan). En face imaging at an acquired depth is possible depending on the imaging engine used.

SUMMARY

This disclosure provides a method for measuring characteristics of a sample.

In some embodiments, a method for measuring characteristics of a sample is provided. The method includes the following steps: obtaining an interference spectrum of the sample; transforming the interference spectrum into a temporal interference signal via a Fourier transform, in which the temporal interference signal includes a plurality of coherence wave packets; separating the wave packets; transforming the wave packets into a plurality of interface interference signals via an inverse Fourier transform; and fitting a plurality of factors of the interface interference signals into a model for obtaining refractive indexes, extinction coefficients, and a thickness of the sample.

In one or more embodiments, the interference spectrum is measured by a Michelson interferometer.

In one or more embodiments, the Michelson interferometer includes a broadband light source.

In one or more embodiments, a frequency bandwidth of the broadband light source is approximately $1 \times 10^{14}$ Hz to $1 \times 10^{15}$ Hz.

In one or more embodiments, the method for measuring characteristics of a sample further includes the following step: filtering out parts of the temporal interference signal.

In one or more embodiments, a Hilbert transform is applied to separate an envelope amplitude and a carrier phase.

In one or more embodiments, the number of the wave packets is two, and the interface interference signals include a front interface interference signal and a rear interface interference signal.

In one or more embodiments, the front interface interference signal is formed by the interference of a reference light and a light reflected by a front interface of the sample, and the rear interface interference signal is formed by the interference of the reference light and a light reflected by a rear interface of the sample.

In one or more embodiments, the model includes the following equations:

$$A = G|r_{front}|$$
$$B = G|t_{front} t'_{front} r_{rear}|\exp(-4\pi kfl/c)$$
$$C = \angle\left(\frac{t_{front} t'_{front} r_{rear}}{r_{front}}\right) + 4\pi nfl/c$$

where A is an amplitude spectrum of the front interface interference signal, B is an amplitude spectrum of the rear interface interference signal, and C is phase differences between the two interface interference signals, G is an interferometer response coefficient, $t_{front}$ is a complex transmission coefficient when a light enters the sample, $t_{front}'$ is a complex transmission coefficient when a light exits the sample, $r_{front}$ is a complex reflection coefficient of the front interface of the sample, $r_{rear}$ is a complex reflection coefficient of the rear interface of the sample, n is the refractive index of the sample, k is the extinction coefficient of the sample, l is the thickness of the sample, f is a frequency of a light, and A, B, and C are represented as functions of n, k and l.

In one or more embodiments, G is determined by the following equation:

$$G = 2\eta a_s a_r \sqrt{I_s I_r} e^{i\phi}$$

where $\eta$ is an interference efficiency, $a_s$ is an attenuation factor of a sample light, $a_r$ is an attenuation factor of a reference light, $I_s$ is an incident intensity of the sample light, $I_r$ is an incident intensity of the reference light, and $\phi$ is a phase related to an optical path difference of the reference light and the sample light.

In one or more embodiments, the Gauss-Newton's algorithm is adopted for the model fitting.

In one or more embodiments, the thickness of the sample has a minimum $\lambda_0^2/(2n\Delta\lambda)$, wherein $\lambda_0$ is a center wavelength of a light source, $\Delta\lambda$ is a wavelength bandwidth of the light source, and n is the refractive index of the sample.

In another embodiment, a method for measuring characteristics of a sample is provided. The method includes the following steps: emitting a sample light to a position of the sample for obtaining an interference spectrum of the position of the sample; and analyzing the interference spectrum by performing the aforementioned method for measuring characteristics of a sample to obtain a thickness of the position of the sample.

By separating the wave packets, which correspond different interface interference signals in the temporal interference signal, factors about these interface interference signals can be obtained. Then refractive indexes, extinction coefficients and a thickness of the sample can be obtained by fitting these factors into a model.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically depicted in order to simplify the drawings.

Figure 1:
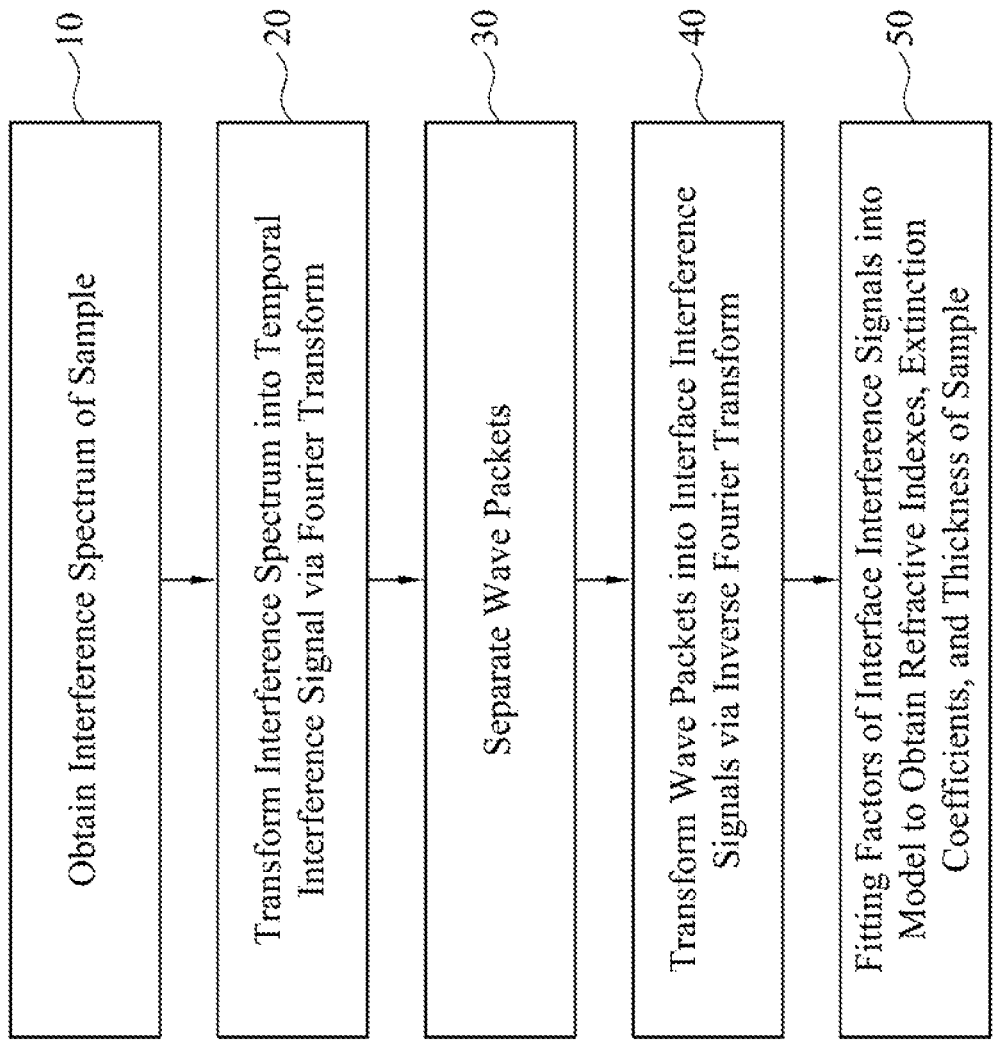
FIG. 1 is a flowchart of a method for measuring characteristics of a sample according to some embodiments of this invention.

FIG. 1 is a flowchart of a method for measuring characteristics of a sample according to some embodiments of this invention. A method for measuring characteristics of a sample 410 (shown in FIG. 4) is provided. The method is based on spectral-domain optical coherence tomography (SD-OCT). The operation steps are described in the followings. Step 10 is obtaining an interference spectrum of the sample 410 (shown in FIG. 4). The interference spectrum can be measured by an optical interferometer system 100 (shown in FIG. 2). The optical interferometer system 100 (shown in FIG. 2) can be a Michelson interferometer.

Figure 2:
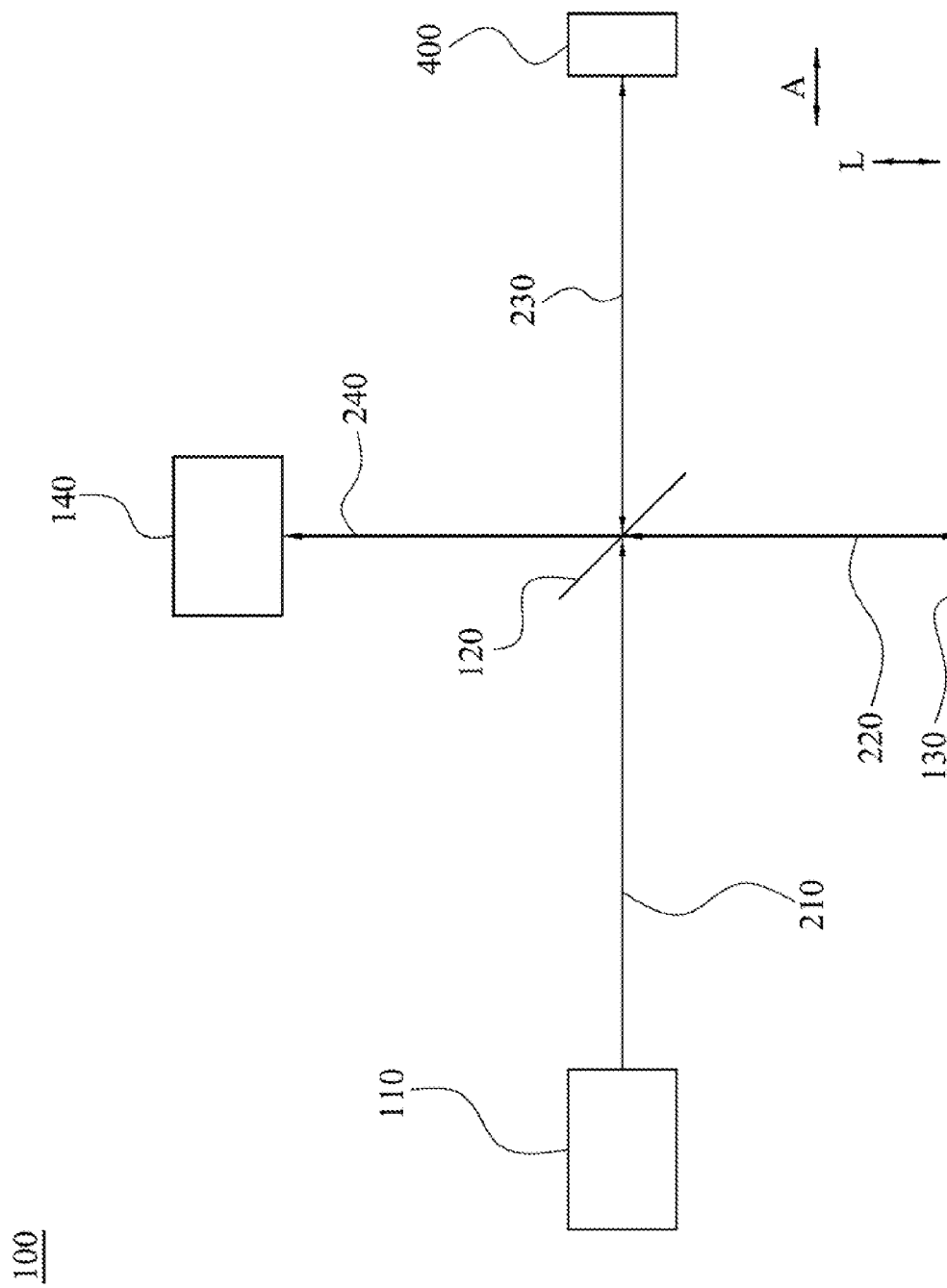
FIG. 2 is a schematic cross-sectional view of an optical interferometer system utilized in some embodiments of this invention.

FIG. 2 is a schematic cross-sectional view of an optical interferometer system utilized in some embodiments of this invention. As shown in FIG. 2, the optical interferometer system 100 includes a light source 110, a beam splitter 120, a reference mirror 130, and a detector 140. The light source 110 emits a source light 210, and the source light 210 is projected into the beam splitter 120 and is separated into a reference light 220 and a sample light 230 by the beam splitter 120. The reference light 220 is projected onto and is reflected by the reference mirror 130, and then the reference light 220 is projected into the beam splitter 120 through the same path. The sample light 230 is projected into a measurement object 400 and is reflected by the measurement object 400, and then the sample light 230 is projected into the beam splitter 120. The reference light 220 and the sample light 230 at the beam splitter 120 interfere with each other and form an interference light 240, and then the detector 140 detects the interference light 240 to form the interference spectrum.

Figure 3:
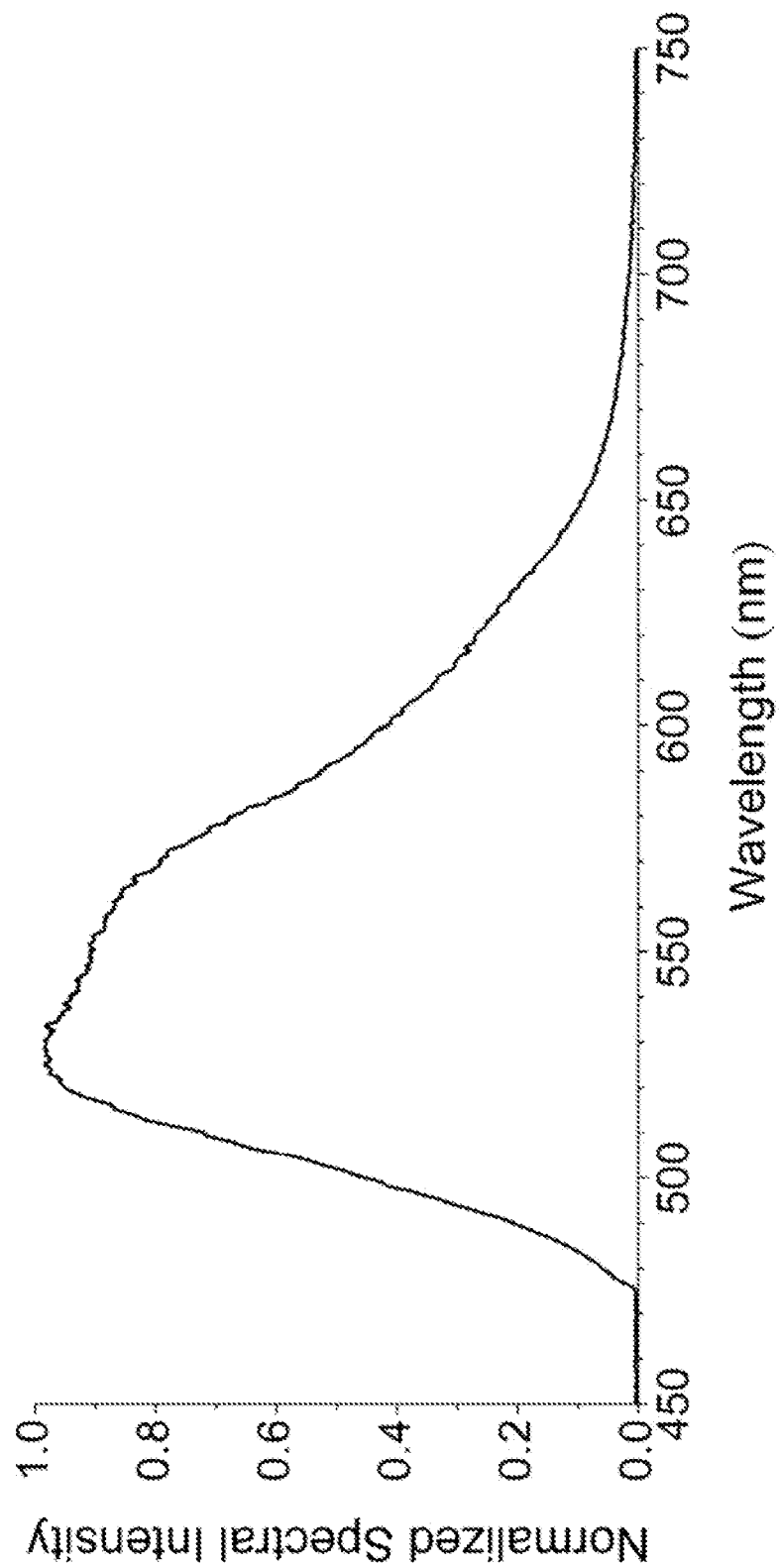
FIG. 3 is a normalized spectral intensity to wavelength figure of a light source according to some embodiments of this invention.

FIG. 3 is a normalized spectral intensity to wavelength figure of the light source according to some embodiments of this invention. Specifically, the light source 110 is a broadband light source. The frequency bandwidth of the light source 110 is approximately larger than $2 \times 10^{13}$ Hz or $1 \times 10^{14}$ Hz to $1 \times 10^{15}$ Hz. More specifically, the light source 110 is a Ce:YAG double-clad crystal fiber (DCF) pumped with a 446-nm laser diode. As shown in FIG. 3, the light source 110 emits a broadband spectrum with a 545-nm center wavelength and a wavelength bandwidth of approximately 90 nm (the frequency bandwidth is approximately $5 \times 10^{14}$ Hz to $6 \times 10^{14}$ Hz), and the shape of the broadband spectrum is similar to the shape of a Gaussian function. In addition, an axial resolution along an axial direction A (shown in FIG. 2) of the optical interferometer system 100 is:

$$l_c \cong 0.44 \cdot \frac{\lambda_0^2}{\Delta \lambda}$$

where $I_c$ is the axial resolution, $\lambda_0$ is the center wavelength, and $\Delta \lambda$ is the wavelength bandwidth. Accordingly, the axial resolution of the optical interferometer system 100 is 1.5 μm (in air).

Specifically, the detector 140 can be a spectrometer. People having ordinary skill in the art can make proper modification to the detector 140 according to their actual needs.

In some embodiments, as shown in FIG. 2, the measurement object 400 includes a sample, and the sample has a planar surface to reflect the sample light 230. The interference spectrum of the sample can be expressed in the following form:

$$S = 2\eta a_s a_r \sqrt{I_s I_r} e^{i\phi} r = Gr$$

where S is the interference spectrum, $\eta$ is an interference efficiency, $a_s$ is an attenuation factor of the sample light 230, $a_r$ is an attenuation factor of the reference light 220, $I_s$ is an incident intensity of the sample light 230, $I_r$ is an incident intensity of the reference light 220, $\phi$ is a phase related to an optical path difference of the reference light 220 and the sample light 230, r is a complex reflection coefficient of the surface, and G is an interferometer response coefficient.

Figure 4:
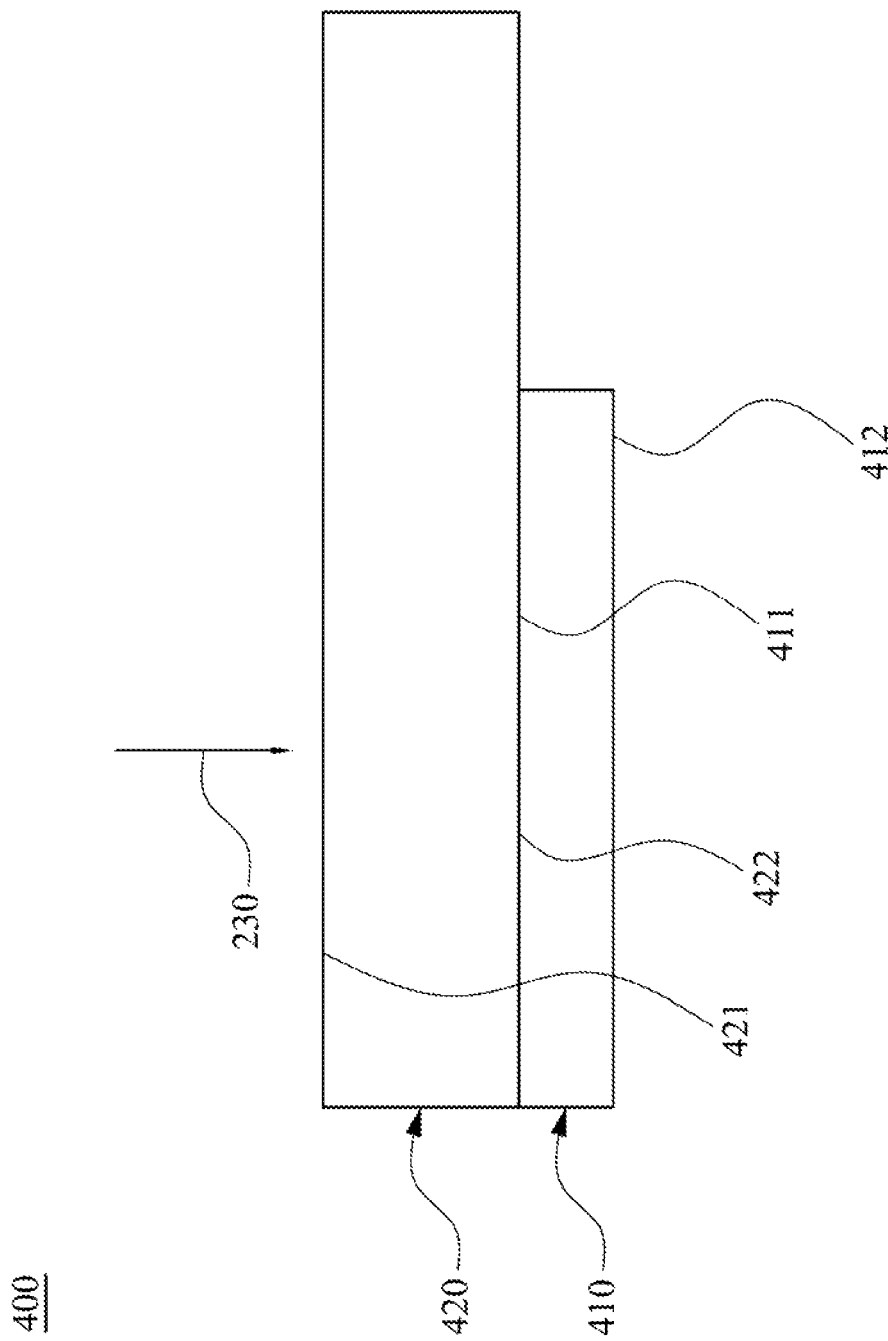
FIG. 4 is a cross-sectional view of the sample disposed on a substrate according to some embodiments of this invention.

FIG. 4 is a cross-sectional view of the sample disposed on a substrate according to some embodiments of this invention. As shown in FIG. 4, the measurement object 400 includes a sample 410 and a substrate 420. The sample 410 has a front interface 411 and a rear interface 412. The substrate 420 has a front surface 421 and a rear surface 422. The sample light 230 is projected into the measurement object 400 from the front surface 421. The sample 410 is disposed on the rear surface 422, and the front interface 411 contacts the rear surface 422.

Specifically, the substrate 420 is transparent. More specifically, the material of the substrate 420 is glass or aluminosilicate glass. The thickness of the substrate 420 is 500 μm. People having ordinary skill in the art can make proper modification to the substrate 420 according to their actual needs.

Step 20 is transforming the interference spectrum into a temporal interference signal via a Fourier transform. The detected interference spectrum is in a spectral domain, and the interference spectrum can be transformed in to a temporal domain via the Fourier transform to form the temporal interference signal.

Figure 5:
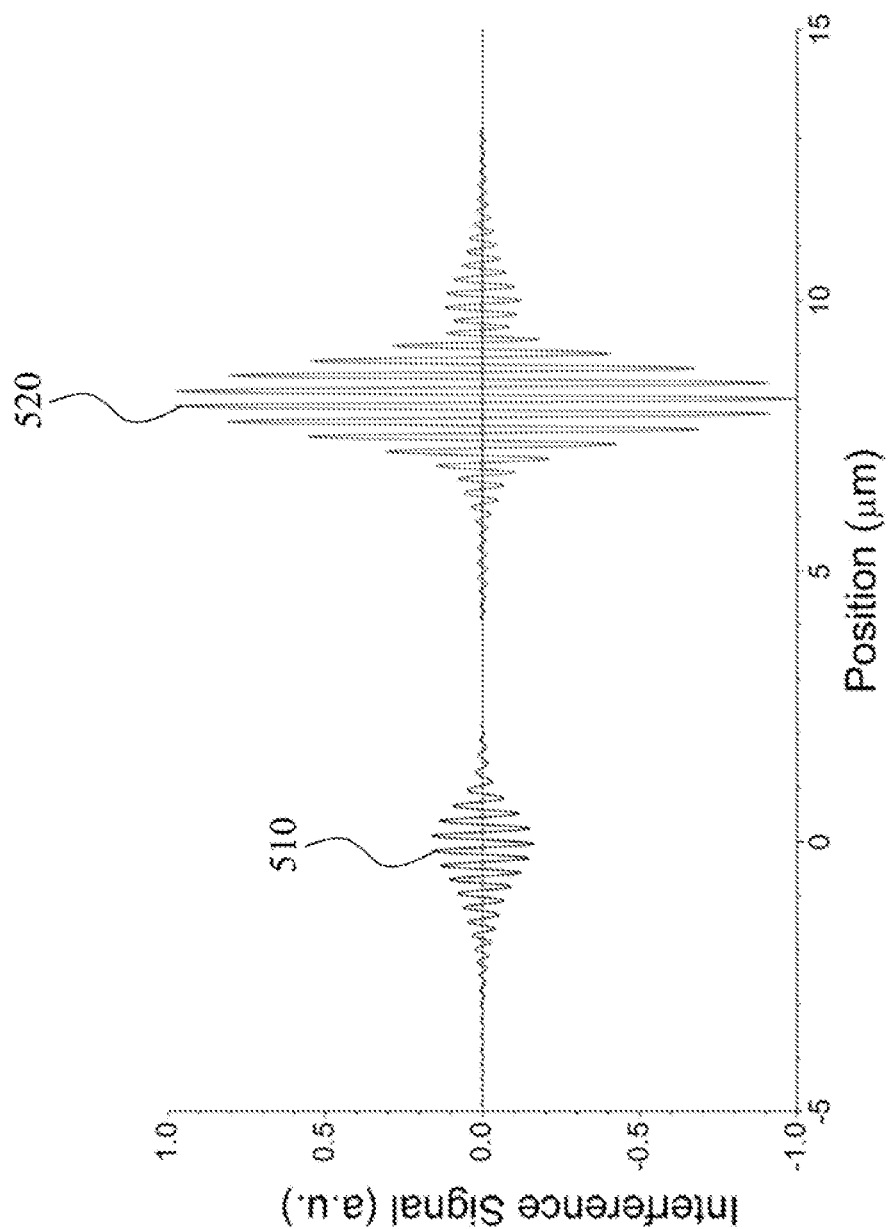
FIG. 5 is a temporal interference signal according to some embodiments of this invention.

FIG. 5 is a temporal interference signal according to some embodiments of this invention. Because speed of light is a constant, a unit of x coordinate of the temporal interference signal can be transformed from time into position. The temporal interference signal includes a plurality of coherence wave packets.

Specifically, the number of the wave packets is two.

Step 30 is separating the wave packets. If the axial resolution $I_c$ is large enough, the wave packets can be identified respectively in the temporal interference signal. In order to enhance the separating ability, parts of the temporal interference signal can be filtered out, and the parts of the temporal interference signal is near zero optical path difference in the temporal domain. In addition, a Hilbert transform can be applied to separate an envelope amplitude and a carrier phase.

Step 40 is transforming the wave packets into a plurality of interface interference signals via an inverse Fourier transform. Specifically, the interface interference signals include a front interface interference signal and a rear interface interference signal. More specifically, as shown in FIG. 2 and FIG. 4, the front interface interference signal is formed by the interference of the reference light 220 and a light reflected by a front interface 411 of the sample 410, and the rear interface interference signal is formed by the interference of the reference light 220 and a light reflected by a rear interface 412 of the sample 410.

The interference spectrum of the sample 410 can be expressed in the following equation:

$$S = G\left[r_{front} + t_{front}t'_{front}r_{rear}\frac{\exp[i4\pi(n+ik)fl/c]}{1 - r_{front}r_{rear}\exp[i4\pi(n+ik)fl/c]}\right]$$

where $t_{front}$ is a complex transmission coefficient when a light enters the sample 410, $t_{front}'$ is a complex transmission coefficient when a light exits the sample 410, $r_{front}$ is a complex reflection coefficient of the front interface 411 of the sample 410, $r_{rear}$ is a complex reflection coefficient of the rear interface 412 of the sample 410, n is a refractive index of the sample 410, k is an extinction coefficient of the sample 410, l is a thickness of the sample 410, and f is a frequency of a light. The first term of the equation corresponds to the front interface interference signal, and the second term of the equation corresponds to the rear interface interference signal.

The equation of the reflection coefficient in the square brackets can be obtained via the summation of a geometric series of amplitudes of multiple reflections. If the denominator is expanded in the equation into a geometric series, then each of the terms in the series represents a reflection among the sum of multiple reflections. In the temporal domain, these terms are separated by a time duration equal to the roundtrip flight time of 2nl/c within the sample 410. Each of these terms in the temporal domain has a temporal width of approximately 1/Δf, where Δf is the frequency bandwidth of the light source 110. These terms are separable provided 1/Δf<2nl/c. As a result of this separation requirement, the method is useful for the sample 410 with a minimum thickness of c/(2nΔf)=$\lambda_0^2$/(2nΔλ), where $\lambda_0$ is the center wavelength and Δλ is the wavelength bandwidth. In the embodiments, $\lambda_0$=545 nm, Δλ=90 nm, n~1.6, the minimum thickness of the sample 410 is approximately 1 μm.

As shown in FIG. 5, the wave packet 510 corresponds to the front interface interference signal, and the wave packet 520 corresponds to the rear interface interference signal.

Figure 6:
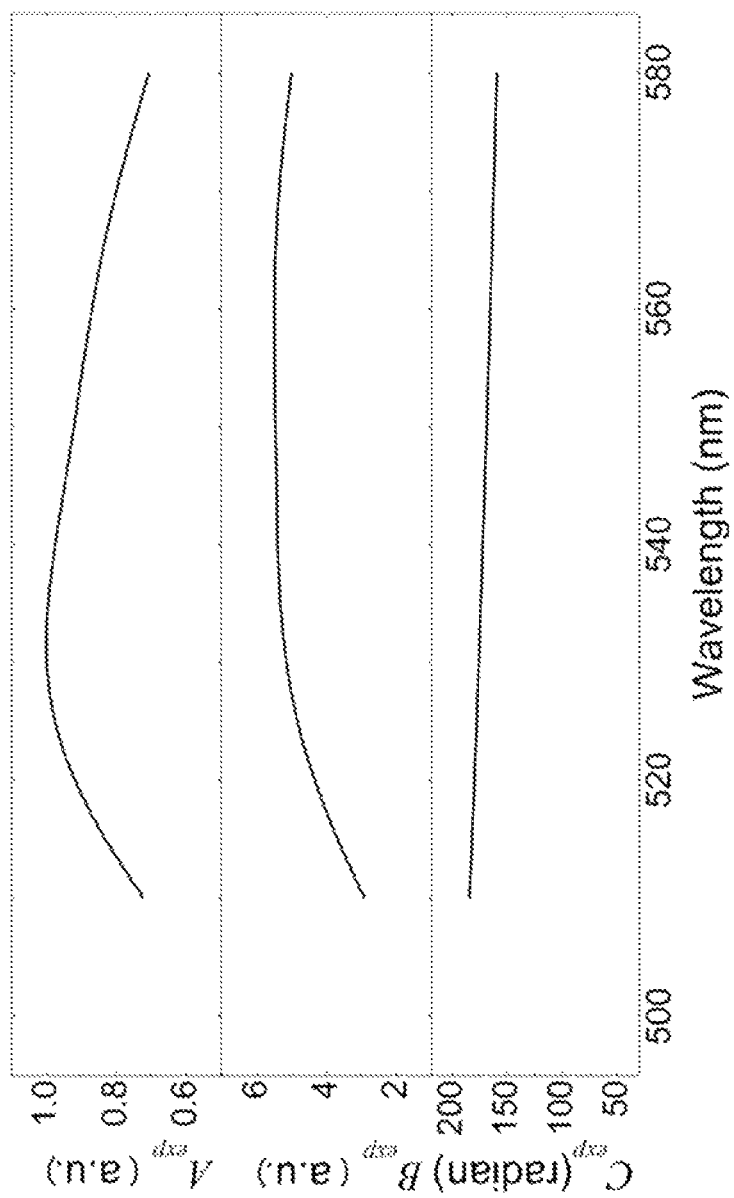
FIG. 6 is amplitude spectrums of a front interface interference signal and a rear interface interference signal and phase differences between the two interface interference signals according to one embodiment of this invention.

The front interface interference signal has an amplitude and a phase for each wavelength (or frequency), and the rear interface interference signal has an amplitude and a phase for each wavelength (or frequency). Accordingly, phase differences between the two interface interference signals for different wavelengths (or frequencies) are formed. As shown in FIG. 6, which is amplitude spectrums of the front interface interference signal and the rear interface interference signal and phase differences between the two interface interference signals according to some embodiments of this invention. $A_{exp}$ is a measured value of the amplitude of the front interface interference signal, $B_{exp}$ is a measured value of the amplitude of the rear interface interference signal, and $C_{exp}$ is a measured value of the phase difference.

Step 50 is fitting a plurality of factors of the interface interference signals into a model for obtaining refractive indexes n, extinction coefficients k, and a thickness l of the sample. Specifically, there are four factors, that is the amplitudes A and B and the phases of the front interface interference signal and the rear interface interference signal, of the sample 410 for each wavelength (or frequency). Therefore, four parameters associated with the sample 410 (shown in FIG. 4) can be obtained for each wavelength (or frequency) in one measurement, so it is possible to obtain the refractive indexes n, the extinction coefficient k, the thickness l of the sample 410 (shown in FIG. 4) in one measurement.

The model includes the following equations:

$$A = G|r_{front}|$$

$$B = G|t_{front}t'_{front}r_{rear}|\exp(-4\pi kfl/c)$$

$$C = \angle\left(\frac{t_{front}t'_{front}r_{rear}}{r_{front}}\right) + 4\pi nfl/c$$

where A is an amplitude spectrum of the front interface interference signal, B is an amplitude spectrum of the rear interface interference signal, and C is phase differences between the two interface interference signals. In additional, A, B, and C are represented as functions of n, k and l.

The Gauss-Newton's algorithm can be adopted for the model fitting, and the algorithm is described in the following. First an appropriate initial guess values of (n, k, l) is put in the model. Then the increment vector (δn, δk, δl) of each wavelength can be determined with the following equation:

$$\begin{pmatrix} \delta n \\ \delta k \\ \delta l \end{pmatrix} = \begin{pmatrix} \frac{\partial A}{\partial n} & \frac{\partial A}{\partial k} & \frac{\partial A}{\partial l} \\ \frac{\partial B}{\partial n} & \frac{\partial B}{\partial k} & \frac{\partial B}{\partial l} \\ \frac{\partial C}{\partial n} & \frac{\partial C}{\partial k} & \frac{\partial C}{\partial l} \end{pmatrix}^{-1} \begin{pmatrix} A_{exp} - A \\ B_{exp} - B \\ C_{exp} - C \end{pmatrix}$$

where $A_{exp}$, $B_{exp}$ and $C_{exp}$ are measured values of A, B and C. Since the thickness l is known to be wavelength-independent, the actual increment of l for each iteration is the average value of δl derived from the above equation for each wavelength. With the initial condition described above and an accuracy requirement of, for example, 1%, the result usually converges within 100 iterations.

As shown in FIG. 2 and FIG. 4, for optical thickness of sample 410 larger than half wavelength of the sample light 230, phase ambiguity problem may occur. This ambiguity comes from the fact that the phase retrieved with SD-OCT is always within the principal $2\pi$ range. A continuous phase spectrum (proportional to the thickness of the sample 410) can be obtained via the employment of a phase unwrapping method. Unwrapped phase spectrum has a $2\pi m$ phase shift from the actual phase, where m is an unknown integer, and:

$$C_{exp}(m)=C_{unwrapped}+2\pi m$$

where $C_{unwrapped}$ is the continuous phase spectrum directly obtained from the detection. This ambiguity problem can be solved by using multiple wavelengths for the detection. It is clear that the mean square error (MSE) of the model increases with incorrect m selection. So, the ambiguity can be resolved by performing the parameter optimization for different m value, and searching for the m value which gives the minimum MSE. The MSE to be considered in this case is defined as:

$$MSE(m) = \left\{ \frac{1}{N} \sum_{j=1}^{N} \left[ \left( \frac{A_{exp}^j - A^j}{A_{exp}^j} \right)^2 + \left( \frac{B_{exp}^j - B^j}{B_{exp}^j} \right)^2 + \left( \frac{C_{exp}^j - C^j}{C_{exp}^j} \right)^2 \right] \right\}^{\frac{1}{2}}$$

where N is the number of data points in the frequency domain, and the superscript j specifies the discrete frequencies within the frequency bandwidth of the light source 110. $m_0$ is defined as the m gives the minimum MSE, $C_{exp}=C_{unwrapped}+2\pi m_0$.

Figure 7A:
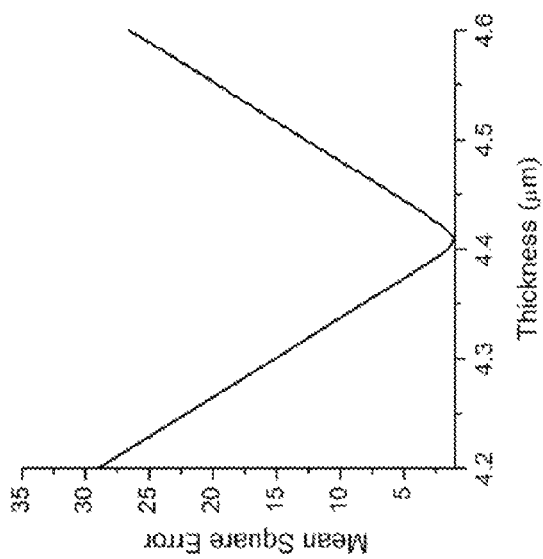
FIG. 7A is a refractive index to wavelength figure of the sample according to one embodiment of this invention.
Figure 7B:
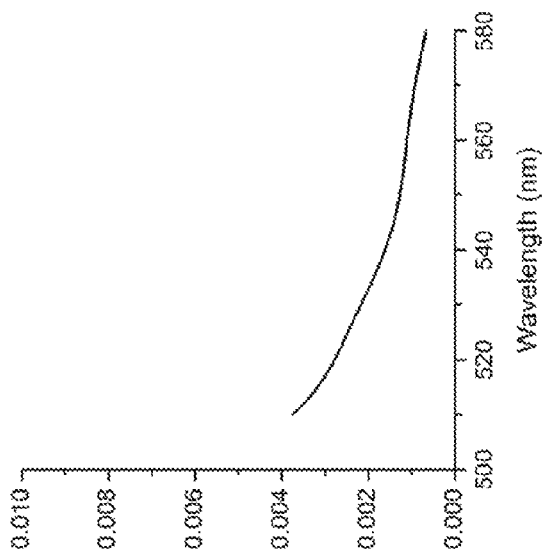
FIG. 7B is an extinction coefficient to wavelength figure of the sample according to one embodiment of this invention.
Figure 7C:
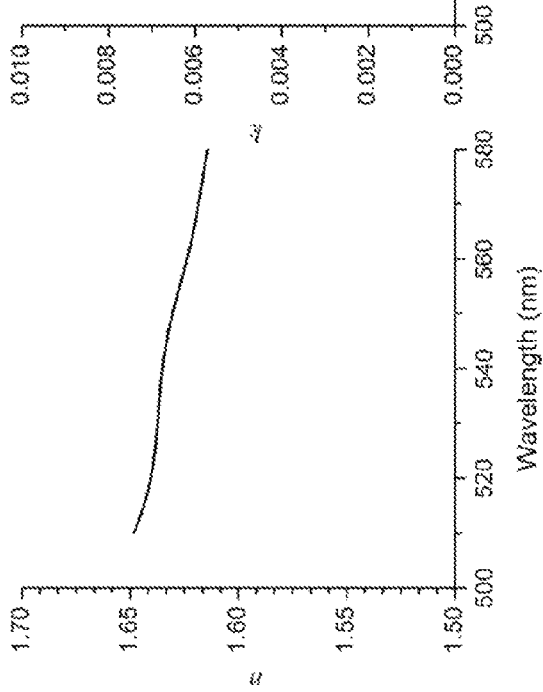
FIG. 7C is a mean square error (MSE) to thickness figure of the sample according to one embodiment of this invention.

FIG. 7A is a refractive index to wavelength figure of the sample according to one embodiment of this invention. FIG. 7B is an extinction coefficient to wavelength figure of the sample according to one embodiment of this invention. FIG. 7C is a mean square error (MSE) to thickness figure of the sample according to one embodiment of this invention. After the aforementioned calculation, the refractive indexes n, the extinction coefficients k, the thickness l of the sample 410 (shown in FIG. 4) can be obtained. The thickness l of sample 410 is the l gives the minimum MSE.

Figure 8:
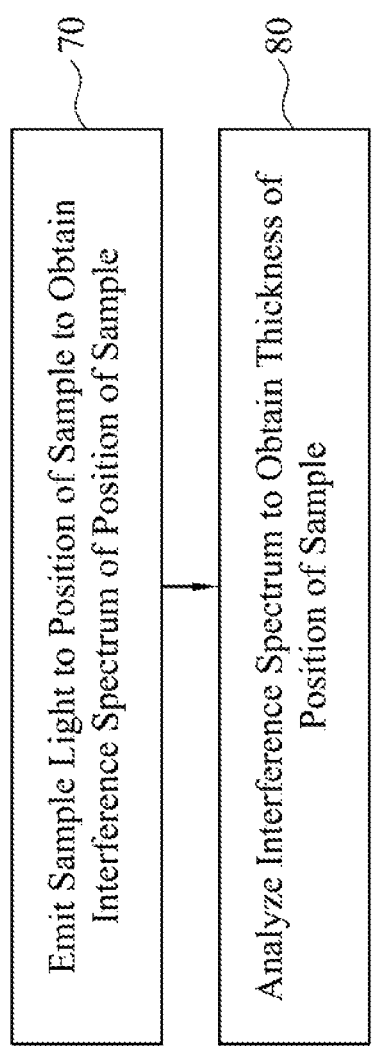
FIG. 8 is a flowchart of the method for measuring characteristics of a sample according to some embodiments of this invention.

FIG. 8 is a flowchart of the method for measuring characteristics of a sample according to some embodiments of this invention. As shown in FIG. 2, FIG. 4, and FIG. 8, another method for measuring characteristics of a sample 410 is provided. The method can measure a shape or a structure of sample 410. The operation steps is described in the followings. Step 70 is emitting a sample light 230 to a position of the sample for obtaining interference spectrum of the position of the sample 410.

Step 80 is analyzing the interference spectrum by performing the method of FIG. 1 to obtain thickness of the position of the sample. Step 70 and Step 80 can be repeated several times, and the positions where the sample light 230 is emitted is distributed along a lateral direction L perpendicular to the axial direction A. After the thicknesses of positions of the sample 410 distributed along the lateral direction L are obtained, the shape or the structure of sample 410 is obtained as well.

By separating the wave packets in the temporal interference signal, which correspond different interface interference signals, factors about these interface interference signals can be obtained. Then refractive indexes, extinction coefficients and a thickness of the sample can be obtained by fitting these factors into a model.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C. §112, 6th paragraph. In particular, the use of "step of" in the claims herein is not intended to invoke the provisions of 35 U.S.C. §112, 6th paragraph.

What is claimed is:

1. A method for measuring characteristics of a sample, the method comprising:
    obtaining an interference spectrum of the sample, wherein the interference spectrum is measured by an interferometer, the interferometer includes a broadband light source, the light source emits a broadband spectrum with a shape similar to a shape of a Gaussian function;
    transforming the interference spectrum into a temporal interference signal via a Fourier transform, wherein the temporal interference signal includes a plurality of coherence wave packets;
    separating the wave packets;
    respectively transforming the separated wave packets into a plurality of interface interference signals via an inverse Fourier transform; and
    fitting a plurality of factors of the interface interference signals into a model for obtaining refractive indexes for different wavelengths, extinction coefficients for different wavelengths, and a thickness of the sample.

2. The method of claim 1, wherein the interference spectrum is measured by a Michelson interferometer.

3. The method of claim 1, wherein a frequency bandwidth of the broadband light source is approximately $1 \times 10^{14}$ Hz to $1 \times 10^{15}$ Hz.

4. The method of claim 1, further comprising:
    filtering out parts of the temporal interference signal.

5. The method of claim 1, wherein a Hilbert transform is applied to separate an envelope amplitude and a carrier phase.

6. The method of claim 1, wherein the number of the wave packets is two, and the interface interference signals include a front interface interference signal and a rear interface interference signal.

7. The method of claim 6, wherein the front interface interference signal is formed by the interference of a reference light and a light reflected by a front interface of the sample, and the rear interface interference signal is formed by the interference of the reference light and a light reflected by a rear interface of the sample.

8. The method of claim 6, wherein the model includes the following equations:

$$A = G|R_{front}|$$

$$B = G|t_{front}t'_{front}r_{rear}|\exp(-4\pi kfl/c)$$

-continued $$C = \angle\left(\frac{t_{front}t'_{front}r_{rear}}{r_{front}}\right) + 4\pi nfl/c$$

wherein A is an amplitude spectrum of the front interface interference signal, B is an amplitude spectrum of the rear interface interference signal, and C is phase differences between the two interface interference signals, G is an interferometer response coefficient, $t_{front}$ is a complex transmission coefficient when a light enters the sample, $t_{front}'$ is a complex transmission coefficient when a light exits the sample, $r_{front}$ is a complex reflection coefficient of the front interface of the sample, $r_{rear}$ is a complex reflection coefficient of the rear interface of the sample, n is the refractive index of the sample, k is the extinction coefficient of the sample, l is the thickness of the sample, f is a frequency of a light, and A, B, and C are represented as functions of n, k and l.

9. The method of claim 8, wherein G is determined by the following equation:

$$G = 2\eta a_s a_r \sqrt{I_s I_r} e^{i\phi}$$

wherein $\eta$ is an interference efficiency, $a_s$ is an attenuation factor of a sample light, $a_r$ is an attenuation factor of a reference light, $I_s$ is an incident intensity of the sample light, $I_r$ is an incident intensity of the reference light, and $\phi$ is a phase related to an optical path difference of the reference light and the sample light.

10. The method of claim 8, wherein the Gauss-Newton's algorithm is adopted for the model fitting.

11. The method of claim 1, wherein the thickness of the sample has a minimum $\lambda_0^2/(2n\Delta\lambda)$, wherein $\lambda_0$ is a center wavelength of a light source, $\Delta\lambda$ is a wavelength bandwidth of the light source, and n is the refractive index of the sample.

12. A method for measuring characteristics of a sample, the method comprising:
emitting a sample light to a position of the sample for obtaining an interference spectrum of the position of the sample; and
analyzing the interference spectrum by performing the method of claim 1 for obtaining a thickness of the position of the sample.

* * * * *